(12) United States Patent
Schnell

(10) Patent No.: US 8,251,973 B2
(45) Date of Patent: Aug. 28, 2012

(54) MEDICAL DEVICES AND METHODS FOR ASSISTING IN SUB-SCAB ACCESS

(75) Inventor: William J. Schnell, Libertyville, IL (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 12/945,485

(22) Filed: Nov. 12, 2010

(65) Prior Publication Data

US 2011/0060263 A1   Mar. 10, 2011

Related U.S. Application Data

(62) Division of application No. 12/390,180, filed on Feb. 20, 2009.

(51) Int. Cl.
*A61M 31/00* (2006.01)
(52) U.S. Cl. .......... 604/500; 604/263; 606/131
(58) Field of Classification Search ......... 604/263, 604/264, 272, 273, 274, 500; 606/131; 206/363, 206/365, 366, 367, 438, 439
See application file for complete search history.

(56) References Cited

U.S. PATENT DOCUMENTS

| | | | | |
|---|---|---|---|---|
| 1,501,324 | A * | 7/1924 | Eisele | 206/366 |
| 5,928,215 | A * | 7/1999 | Caizza et al. | 604/411 |
| 6,726,649 | B2 | 4/2004 | Swenson et al. | |
| 6,736,798 | B2 | 5/2004 | Ohkubo et al. | |
| 2001/0037954 | A1 | 11/2001 | Schmidt et al. | |
| 2004/0153038 | A1 | 8/2004 | Guala | |
| 2005/0199099 | A1 | 9/2005 | Schaeffer | |

FOREIGN PATENT DOCUMENTS

WO   WO 2008/005441 A2   1/2008

* cited by examiner

*Primary Examiner* — Kevin C Sirmons
*Assistant Examiner* — Kami A Bosworth

(57) ABSTRACT

Device and methods for separating a scab from a vascular access site are disclosed. The devices include providing a scab separation device having a point for initial separation of a portion of a scab from a patient's flesh, and a series of inclined surfaces leading from the point to lift and separate the scab from the access site. The scab separation device is provided with a cover so that the device is maintained as sterile. In a preferred embodiment, the scab separation device is provided as a set or assembly with a needle or needle set and, in a more preferred embodiment, the scab separation device cover is also used as a cover for a needle to maintain sterility both of an operative end of the separation device and of the needle.

15 Claims, 3 Drawing Sheets

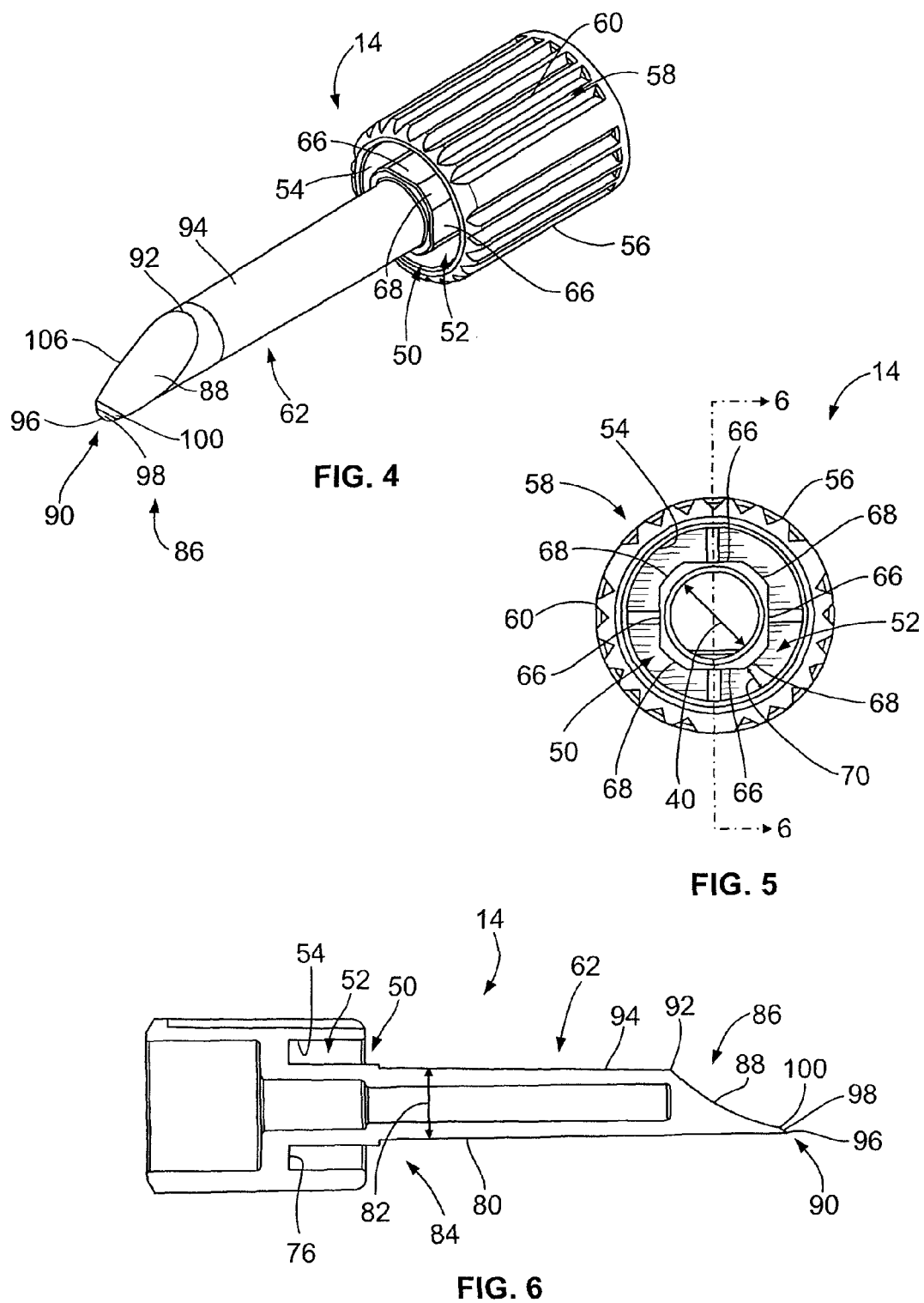

MEDICAL DEVICES AND METHODS FOR ASSISTING IN SUB-SCAB ACCESS

CROSS REFERENCE TO RELATED APPLICATION

This application is a Divisional of U.S. patent application Ser. No. 12/390,180, entitled "MEDICAL DEVICES AND METHODS FOR ASSISTING IN SUB-SCAB ACCESS", filed Feb. 20, 2009.

FIELD OF THE INVENTION

The invention relates to a device for accessing a patient's arterio-venous or vascular system and, in particular, to such a device where a pre-existing scab is located at an access site for the vascular system.

BACKGROUND

As used herein, the term 'scab' refers to a hardened or solidified crust produced by a cutaneous sore, wound, ulcer, or pustule. For instance, a scab or scab portion principally refers to blood components that have been released from a patient and, subsequently, hardened or solidified into a crust-like deposit on or proximate the patient's skin.

It is commonly desired to enable sub-scab access, that is, access below the scab or to the area below a portion of the scab. In a number of medical procedures, a single site or access point is used and re-used for access to a patient's vascular or arterio-venous system. One example of such procedure is for extracorporeal blood treatment such as hemodialysis. Alternatively, there are many times where re-use of a particular access site is desired, such as for repeated drawing of blood, blood transfusions, provision of medicaments, or other blood treatment procedures.

During such described procedure, a particular access site is located. It is noted that were a plurality of proximate sites used, such can damage or destroy parts of the vascular system, often referred to as a section of the vascular system "collapsing." Access is gained percutaneously via a needle, for instance, so that blood in the vascular system can be withdrawn and/or so that fluid (including blood, such as during hemodialysis) can be returned or added to the patient's bloodstream.

When the needle is removed, it is common for the access site to be closed by application of pressure. Closing of the vascular access site is necessary because a patient's blood pressure is higher than that of ambient pressure, and, regardless of the use of the site to infuse fluid or to draw fluid, the vascular pressure will force blood out of the vascular access site.

In any event, the vascular access site deposits blood fluid and/or other fluid at the access site, fluid which forms a scab when contacted by air. Principally, the scab may comprise blood platelets. As a coagulation mechanism, the platelets recognize the formation of the access site, such as by a needle, as an injury. The platelets respond to this by adhering to each other and to the edges of the injury, such as the opening formed in the vascular system, as well as to the patient's flesh between the vascular system access site and the surface of the skin. The platelets then coagulate, which includes retracting or shrinking across the injury to stop the loss of blood and to form a barrier to infection. Finally, in the presence of air (as opposed to a blood clot), the platelets harden to form the scab.

In order to access the vascular site a subsequent time, the scab must be overcome. Obviously, a medical technician could attempt to bypass the scab, working along an edge thereof; however, this is unlikely to be very effective, yet is nonetheless likely to be tedious. Generally, a medical technician or patient, as in home hemodialysis, simply removes, in crude fashion, the scab from the access site. For instance, the technician may use a sterile needle tip or sterile tweezers to pick at the edge of the scab to dislodge and lift the scab from the flesh surrounding the access site.

It should be emphasized that the access site is a direct portal into the patient's bloodstream. Use of a non-sterile device or second use of a sterile device for removing the scab is virtually tantamount to injecting bacteria into a patient's bloodstream. If an access needle tip is used, the scab is certainly not sterile, and subsequent insertion of the needle tip into the patient's vascular system after picking at the scab is similarly injecting potential pathogens into a patient's bloodstream. The needle may be dulled or deformed by use as a picking device, making the insertion more painful or damaging to vascular tissue. Finally, particulate matter, either non-sterile scab material or non-sterile skin material, may be carried with the needle tip into the bloodstream.

PCT application WO2008/005441, assigned to JMS Company, LTD ("the JMS application") discloses a "Needle Cover with Site Preparation Tip." While a needle and needle set typically have a cover to protect the needle (both for sterility and to maintain a sharp edge for non-blunt needles), the JMS application teaches a "needle cover shaped for removing scabs" for use in assisting with removal of the scab. It further teaches to leave the needle cover in place on the needle set during scab removal. Because a typical needle set for constant site cannulation is a minimum six inches long, this leaves the user with the choice either of manipulating the entire needle set (including the long, tail-like associated tubing and connectors) in order to use the "tip" and trying to keep the friction fit cover from disconnecting from the needle set, or of purposefully removing the needle cover from the needle set (in order to have a more finely controllable site preparation tip) which breaks sterility of the needle and renders it unsafe for cannulation into the patient.

The JMS application describes the needle cover including tip being formed of polyurethane, polyethylene, polypropylene, and the like, each of which is a relatively soft material. The softness of the material is necessary so that the cover can be releasably secured, frictionally, with the needle hub. The result is that the tip itself is formed of a soft material. As the entire product (i.e., needle set with cover and tip) would be packaged in a paper/plastic wrapper, the soft tip is susceptible to being blunted or damaged during packaging, shipping, storage, and other handling and generally not ideal for trying to lift out a hardened scab.

Additionally, sterility of the tip is broken when the outer wrapper of the needle set is opened. In a typical procedure, the needle set would be removed from its package well before removal of the scab, and would then be placed proximate the patient's arm on an unsterile field along with the many other items needed for the cannulation procedure. The needle cover maintains sterility of the cannulating needle while the the access site is prepared, which is after, for instance, an antiseptic cleansing of the area. In other words, the clinician must make a choice between removing the needle set of the JMS application from the package and leaving it exposed while cleaning the access site, or cleaning the site and then handling the non-sterile exterior wrapping of the needle set to open the needle set during which time the access site is exposed. Notably, this fact is resonated by the JMS application stating that the cover should be removed from the needle, and the needle inserted "without delay," yet the JMS application fails to appreciate that the preparation tip itself faces similar risks, since it is used to dig around the constant site opening to the patient's circulatory system. In fact, while the JMS application states the order of steps may be modified, there are constrictions on how they may be done, at least such that choices must be made between what sterility is maintained and what is foregone.

Accordingly, there has been a need for an improved device to enable the removal or dislodgement of a scab to access a vascular site, the device preferably being sterile.

SUMMARY

In accordance with an aspect of the present invention, a scab separation device is disclosed including an operative portion having a terminal point for initial separation of a scab from a patient's flesh, and a lifting surface extending from the terminal point for assisting in separation of the scab from the patient's flesh, the separation device also including a grip portion for manipulating the scab separation device.

In some forms, the lifting surface includes a series of surfaces of differing inclinations for assisting in scab separation. The series of surfaces may include a first surface, and a second surface, wherein at least one of the first and second surfaces includes an inclined surface.

In some forms, the terminal point and lifting surface define a separation edge for focusing stress at a junction between the scab and the patient's flesh.

The separation device further includes a cover for maintaining sterility of the operative portion prior to use. The grip portion of the separation device may be connected to the operative portion by a hub portion, and the cover may be removably securable over the operative portion and with the hub portion. The hub portion and cover may have cooperating structure for removably securing the hub portion with the cover.

In another aspect, a vascular access set is disclosed including an access needle set having a needle for insertion into an access site of a patient, and having a body for holding the needle, and including a scab separation device for assisting in accessing a vascular access site of the patient.

In some forms, the needle set of the vascular access set further includes a tubing communicating with the body for fluid communication from the patient through the needle and into the tubing.

In some forms, the needle set of the vascular access set includes an arterio-venous fistula.

In some forms, the vascular access set further includes at least a first cover for maintaining sterility of the scab separation device. The first cover may be securable over an operative end of the scab separation device and the needle for maintaining sterility thereof. The scab separation device may include a grip portion connected to the operative portion by a hub portion, and the cover may be removably securable over the operative portion and with the hub portion.

In some forms, the scab separation device of the vascular access set includes an operative portion having a terminal point for initial separation of a scab from a patient's flesh, and a lifting surface extending from the terminal point for assisting in separation of the scab from the patient's flesh. The scab separation device may include a grip portion for manipulating the scab separation device. The lifting surface may include a series of surfaces of differing inclinations for assisting in scab separation. The series of surfaces may include a first surface, and a second surface, wherein at least one of the first and second surfaces includes an inclined surface.

In some forms of the scab separation device of the vascular access set, the terminal point and lifting surface define a separation edge for focusing stress at a junction between the scab and the patient's flesh.

In a further aspect, a vascular access assembly is disclosed comprising a needle set, which includes a needle, a body having a first end for supporting and manipulating the needle, and a fluid communicating tube connected to a body second end, a scab separation device having an operative portion, and a cover member removably securable with both the needle set and the scab separation device to maintain sterility of the needle and operative portion.

In some forms, the scab separation device of the vascular access assembly includes a hub portion, and the cover member may be frictionally engaged or retained with the hub portion and the body of the needle set. The needle set of the vascular access assembly may include an arterio-venous fistula.

In another aspect, a method of providing sub-scab access is disclosed comprising the steps of providing a sterile scab separation device within a sterility cover, preferably such cover is reversibly attached to a device for cannulating said access site, separating the scab separation device and a sterility cover, directing a terminal point of the scab separation device against an interface between a scab and the patient's flesh at an access site, and separating at least a portion of the scab from the patient's flesh at the access site.

In some forms, the method includes the factory step of frictionally securing the scab separation device with the sterility cover prior to use.

In some forms, the step of separating a least a portion of the scab includes lifting the scab away from the access site via a lifting surface formed proximate the terminal point on the scab separation device.

In some forms, the step of separating the scab separation device includes utilizing a grip portion, the method further including manipulating the scab separation device via the grip portion.

In some forms, the step of providing the scab separation device includes providing a series of surfaces of differing inclinations thereon, and the step of separating at least a portion of the scab includes inserting the scab separation device under the scab whereby the series of surfaces lifts the scab to assist in scab separation. The step of providing a series of surfaces may include providing a first surface and a second surface, at least one of the first and second surfaces being an inclined surface.

In some forms, the method further includes providing a separation edge on the scab separation device for focusing stress at a junction between the scab and the patient's flesh.

In some forms, the method further includes providing the scab separation device with a hub portion, and maintaining the scab separation device with the cover with cooperating structure between the hub and the cover.

In some forms, the method further includes the step of releasably securing the cover with a needle set including a needle at an end opposite the scab separation device. The method may further include providing the needle set with a tubing connected for fluid communication from the patient through the needle and into the tubing. The needle set may include an arterio-venous fistula. The method may include the steps of providing a first cavity portion in the cover for receiving the scab separation device therein, providing a second cavity portion n the cover for receiving the needle therein, and providing a barrier between the first and second cavity portions to at least partially maintain sterility therebetween when one of the scab separation device or needle is removed exposing its respective cavity portion to the environment.

BRIEF DESCRIPTION OF THE DRAWINGS

In the Figures.

FIG. 4 is an enlarged perspective view of the pick device showing a grip, an operative portion, and structure for maintaining the pick device on the cap;

FIG. 5 is a front elevation view of the pick device showing the structure for maintaining the pick device on the cap; and FIG. 6 is a cross-sectional view of the pick device taken along the line 6-6 of FIG. 5 and showing a contour of the pick device operative portion.

DETAILED DESCRIPTION

Figure 1:
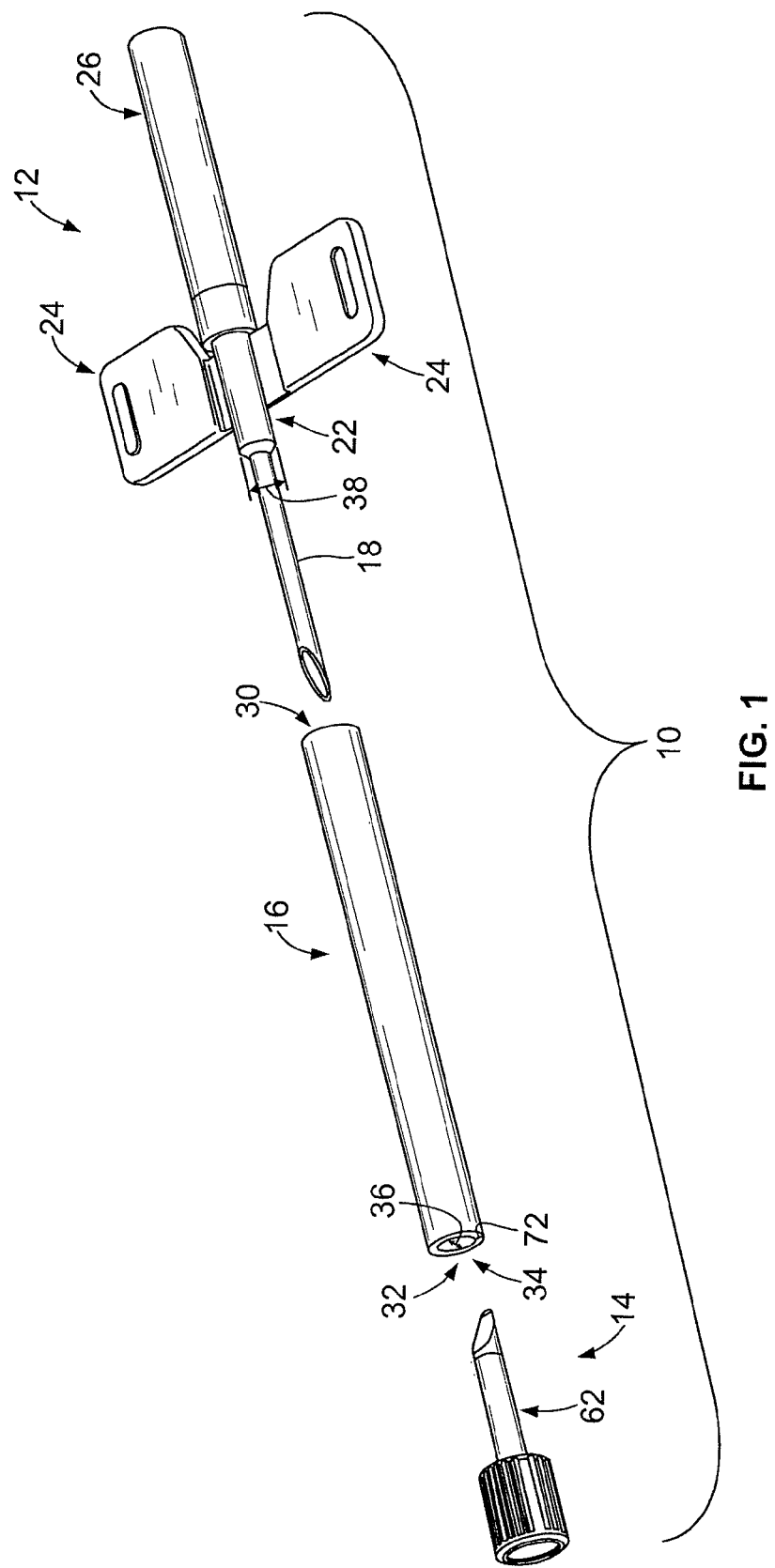
FIG. 1 is a perspective view of an exploded vascular access assembly of the present invention including a needle set, a pick device for enabling sub-scab access to a vascular site, and a cap securable with the needle set and the pick device to maintain sterility of the assembly components.

Referring initially to FIG. 1, a form of the present invention is shown as a vascular access assembly 10 including a needle set in the form of an arterio-venous fistula or AVF 12, a scab-separation device referred to herein as a pick device 14, a sterility and protector cover device referred to herein as a cap 16 for simultaneously maintaining sterility for the AVF 12 and pick device 14, and a protective shipping sterility cover (not shown). It should be noted that, in its simplest, the scope of the present invention includes each of the pick device 14, in various forms, the vascular access assembly 10 as shown and obvious variants thereof, and methods for providing the pick device 14, separately and independently or jointly.

In the present form of FIG. 1, the AVF 12 is an aterio-venous fistula or AVF such as would be used in extracorporeal blood treatment like hemodialysis. As used herein, the term "needle set" may refer to any needle or cannulated device used for entering and/or piercing the skin to access a sub-surface portion of a patient's body, and mounting structure for the needle. In the present form, the AVF 12 includes a cannula 18 of known construction and configuration, a body 22 for mounting and securing the cannula 18, grips 24 for manipulating the AVF 12 (such as manipulating the cannula 18 for advancement into or removal from a vascular access site), and a fluid conveying tubular set 26 for conveying fluid into or out of the vascular access site. Typically, the vascular access site is a portion of a patient's vascular system and the flesh surrounding the point or region of entry thereto.

The cap 16 in the present form is similar to a standard cap as would normally be associated with the AVF 12. That is, the cap 16 is a generally tubular or frustoconical member having a proximate opening 30 for receiving the cannula 18 therein and for maintaining the sterility of the cannula 18 and a portion of the body 22.

The cap 16 includes a second opening 32, distally located. The distal opening 32 receives and maintains the sterility of the pick device 14.

Figure 2:
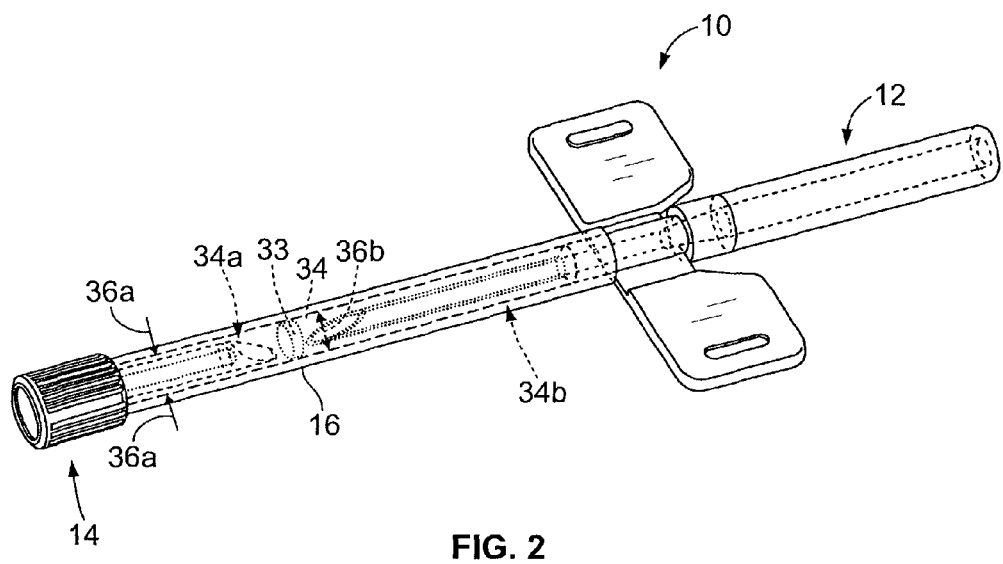
FIG. 2 is a perspective view in partial phantom of the vascular access assembly showing the needle set, the pick device, and the cap assembled in a sterile assembly.
Figure 3:
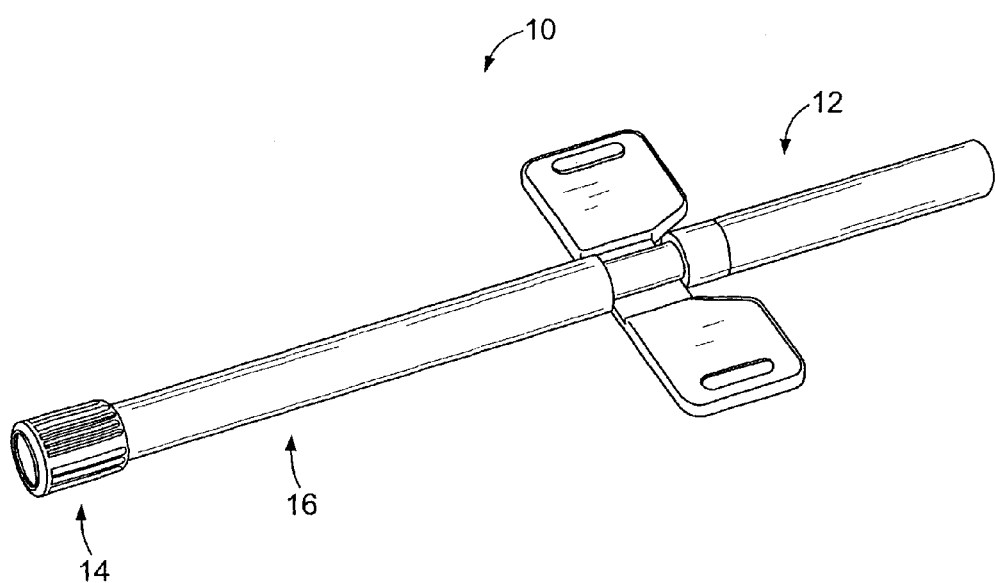
FIG. 3 is a perspective view similar to FIG. 2 showing the assembled vascular access assembly.

Towards these ends, the cap 16 has a central and generally cylindrical cavity 34 (see also FIG. 2) such that both the pick device 14 and body 22 are releasably received therein. The cavity 34, as shown, has a uniform or tapered diameter 36, as such is the simplest construction for extrusion or molding.

However, the cap 16 may be constructed to provide separate cavity portions 34a and 34b, separated by a wall (not shown), and the separate cavity portions 34a, 34b may be configured with different or non-uniform diameters 36a and 36b tailored to the construction of the pick device 14 and the needle body 22. In some forms, a separator 33 separates cavity portions 34a and 34b of the cap 16 for respectively receiving the pick device 14 in cavity portion 34a and receiving the needle 18 and body 22 in cavity portion 34b. The separator 33 may be unitarily molded with the rest of cap 16, preferred for radiation sterilization of vascular access assembly 10, or the separator 33 may be a barrier or piece of open cell foam that allows gas used for gaseous sterilization to pass through but generally provides a tortuous pathway sterility barrier when one of the pick device 14 or body 22 is removed from the cap 16 while the other remains therein. Additionally, other structural features (not shown) may be provided between or within the cap 16 and either or both of the pick device 14 and cannulating needle 18 for maintaining these items sterile or aseptic until scab removal and later, cannulation are performed, such as frangible portions, as is known in the art.

As can be seen, the cap 16 distal opening 32 and pick device 14 provide cooperating and engaging structure for maintaining the pick device 14 together in a sterile arrangement. In a preferred embodiment, the cap 16 is formed of a polymeric material that is slightly resiliently deformable and is suitable for sterilization. In this manner, receipt of the cap 16 with both the pick device 14 and a portion of the AVF 12 is a frictional engagement. That is, the diameter 36 of the cavity 34 in the region of the proximate opening 30 is slightly smaller than a diameter 38 of the body 22 so that the cap 16 is deformed slightly outward. Similarly, diameter 36 of the cavity 34 in the region of the distal opening 32 is slightly smaller than a diameter 40 of a hub portion 50 of the pick device 14 (see FIGS. 4-6).

In greater detail, the cap 16 is received in a somewhat annular cavity 52 of the pick device 14 for securement therewith. The pick cavity 52 is generally defined by an inner surface 54 of a generally cylindrical grip body 56. The grip body 56 includes an external surface 58 including grip structure 60 promoting the manipulation of the pick device 14 in use. The pick cavity 52 surrounds the hub portion 50.

The hub portion 50 and pick cavity 52 preferably allow both for outward deformation of the cap 16 and for inward compression to maintain an operative portion, generally represented as 62, of the pick device 14 as sterile, when sterilized by a gas such as ETO. Towards this end, the hub portion 50 is shaped as a cylindrical body with truncated portions. To be specific, the hub portion 50 includes one or more flats 66 generally positioned tangentially of a central longitudinal axis of the cap 16 when received on the hub portion 50. Spanning between and connecting the flats 66 are arced or circular portions 68. The circular portions 68 are radially (or, more precisely, diametrally) sized relative to the cap diameter 36 so that the cap 16, when received on the hub portion 50, is stretched or deformed outwardly, at least in the local region of the circular portions 68. Such flats 66 are not required for heat or radiation forms of sterilization; in the present form, the flats 66 permit gas sterilization, such as by permitting ETO gas to pass through a so-called "tortuous pathway," that is, between the grip body 56, around the end of the cap 16 received in the cavity 52, and between the flats 66 and the inside of the cap 16.

As noted, the cap 16 when received on the hub portion 50, is also in compression, at least in the local region of the hub circular portions 68. To achieve this, a radial distance 70 from the circular portions 68 to the grip body inner surface 54 is at least slightly less than a wall thickness 72 of the cap 16 proximate the distal opening 34 (see FIG. 1). Accordingly, the cap inner diameter 36 is enlarged in the localized region of the circular portions 68, yet is also compressed in such localized regions. The flats 66, noted above, have a smaller radial extent than the cap inner diameter 36 to allow the cap 16 to deform into regions of the flats 66. As can be seen in FIG. 6, it can be seen that the pick cavity 52 includes a terminal wall 76 that defines a stop for receiving the cap 16 therein, and/or serves to define a sterile region, along with the cap 16, surrounding the operative portion 62 of the pick device 14 and within the cap 16.

Preferably, the pick device 14 is formed of a relatively rigid polymeric material suitable for sterilization. In one form, at least the grip body 56 of the pick device 14 may be formed of a material that is slightly flexible to allow the cap 16 to be received within the pick cavity 52. As shown, the pick device 14 may be formed integral as a unitary body; however, the pick device 14 may be formed of a plurality of components.

Focusing now on FIGS. 4 and 6, the pick device 14 includes the aforementioned operative portion 62. As shown, the operative portion 62 includes a stem 80 extending from the hub portion 50 as a generally elongated portion generally along a longitudinal axis. In the preferred embodiment, the stem 80 is a cylindrical portion having a diameter 82 less than a minimal radial dimension of the hub portion 50 so that the stem 80 provides little to no resistance to movement of the cap 16 when received or removed therefrom. In the present embodiment, the stem 80 is slightly tapered to decrease in diameter from a hub end 84 to an application end 86.

The application end 86 is shaped and contoured to assist in removing of a scab, or releasing a portion thereof, from a patient's vascular access site. The application end 86 includes a curvate lifting surface 88 extending in a generally parabolic manner from a tip 90 to a rearward point 92 along a side 94 of the stem 80. The tip 90 preferably includes a terminal point 96 leading to a series of inclined surfaces including a first small chamfer surface 98 leading to a second small chamfer surface 100 itself leading to the curvate surface 88. As constructed, the terminal point 96 is relatively small to assist in initial separation and lifting of a portion of the scab from the patient's access site. Once initial separation is achieved, each of the first and second chamfers 98, 100 may be used to wedge the application end 96 under the scab, thereby lifting the scab. Additionally, the application end 96 and, in specific, the chamfers 98, 100 flare outwardly so that the initial separation is widened by gentle forcing of the application end 86 under the scab. In this manner, the terminal point 96 and chamfers 98, 100 and curvate surface 88 define a separation edge 106 therealong for focusing stress at the junction between the scab and the patient's flesh, as combining to act as a lifting surface.

The first chamfer 98 preferably has a very slight angle of incline, or may have a zero angle incline. The second chamfer 100 is preferably relatively steeply inclined, though also relatively short in extent in the direction of insertion. The curvate surface 88, as shown, begins with a relatively shallow inclination, and slopes upwardly therefrom in parabolic fashion.

It should be noted that the principal desire of the application end 86 and the pick device 14 generally is not to cut intact tissue, instead generally being to prise apart the scab from the surrounding flesh. Accordingly, the separation edge 106 serves to focus and concentrate stress on a small contact area between the scab and the patient's flesh. However, to the extent necessary or desirable, the separation edge 106 may also serve as a cutting edge.

It should be noted that the present embodiment is simply a single form of the invention. The pick device 14 may be provided with a number of configurations and different contours. The pick device 14 may be provided as a singular device, without the needle set 12 for instance. The pick device 14 may be provided in a variety of sizes and configurations for different applications or different requirements for individual patients in the same manner than many medical devices are provided. Desirably, the pick device 14 is provided with any covering that maintains sterility of the pick device 14, so as to avoid use of the pick device 14 in a manner that would promote entrance of bacteria or contaminants into the access site. The pick device 14 may be provided with any type of needle set 12, either as a kit or as an assembly 10 as shown. The cap 16 for maintaining sterility may be used with both the pick device 14 and the needle set 12, or separate sterility-maintenance devices may be provided for each of the needle set 12 and the pick device 14.

In use, the assembly 10 is packaged for a procedure. The packaging is opened and the assembly 10 is removed. While it is anticipated that an access site having a scab thereon is located, the present assembly 10 may be used without an access site having been already used so that no scab is present. Particularly, the pick device 14, as discussed above, is formed of a polymeric material and, thus, is relatively inexpensive.

Once the access site is identified, the pick device 14 is removed from the cap 16 either before and/or after disinfection of the access site. The terminal point 96 is then gently applied at the edge of a scab or, more appropriately, at the juncture between principally scab material and principally flesh surrounding the access site. Once a small portion of the scab is separated from the flesh, the pick device 14 is slowly worked back and forth to concentrate force therefrom at the separation 106. This allows the chamfers 98, 100 to be worked under the scab. During this time, the terminal point 96 continues to follow the underside of the scab to effect continued separation of the scab from the patient's flesh. The shape of the chamfers 98, 100 and the curvate surface 88 act to lift the scab away from the patient's flesh, thus applying tension to a juncture between the scab and the patient's flesh where the two continued to be connected. Once the scab has been removed to an extent necessary for using the AVF needle set 12 at the access site, the pick device 14 may be removed. It is noted that the scab is generally not sterile, and simple lifting of the same allows contaminants such as bacteria to reach the underside of the scab such that replacement of the scab after the needle set 12 is removed from the access site may cause the access site (or bloodstream) to become contaminated or infected. Accordingly, it is preferred that the scab is entirely removed. Alternatively, the scab may simply be cut back to minimize trauma to the surrounding flesh which is essentially slightly torn by scab separation.

A number of benefits of the presently disclosed devices and methods should be recognized, particularly when compared to the prior art and, more particularly, when compared to the JMS application, WO2008/005441. With the present invention, the typical needle set 12 packaging may be removed without affecting the sterility of the pick device operative portion 62 or of the needle 18, while the "tip" of the JMS application is exposed upon package removal. The cap 16 protects the operative portion 62 and its tip 90, as well as the needle 18, at all times prior to removal from both pathogens and from physical damage through the wrapper, while the "tip" and "cover" device of the JMS application is not protected from damage through the associated packaging.

The procedure for the present vascular access assembly 10 allows for minimal time for pathogen or contamination risk. That is, the assembly 10 may be placed in the typical manner proximate the patient's arm with the wrapper or packaging removed. The access site may be cleaned, such as with antiseptic. Immediately after cleaning, the pick device 14 may be removed from the cap 16 and be used for removing or separating the scab from the access site, while the needle 18 remains sterile within the cap 16. Once the access site is prepared for the needle 16, the cap 16 may be removed to expose the needle 18, the needle 18 then being inserted into the patient. The device of the JMS application does not permit this, requiring dwell time during at least some point during this procedure during which pathogens or contaminants can collect.

The present cap 16 may be of a softer material than the needle cannula body 22 and than the pick device hub 50 so that the cap 16 may be releasably and frictionally secured on each. This allows the pick device 14 to be molded as a single unit with its operative portion 62 and tip 90 being of a relatively hard material so that a hard point, and edge (dull to sharp) are provided for removing the scab, while the device of the JMS application is a relatively soft material.

The present pick device 14 can be provided with a surface treatment, such as a lubricant or an antiseptic. Disposed within the cap 16, the operative portion 62 with the surface treatment is not in contact with the cap 16. For the device of the JMS application, any surface treatment applied to the "tip" during assembly or manufacturing will be, essentially, wiped therefrom by the packaging.

The present pick device 14 can be removed from the cap 16 without affecting the sterility of the needle 18. In the JMS application, the cover must remain on the needle, or sterility of the needle is lost or affected. Again, this means the JMS application device must be handled as a unit, including its associated tubing.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A method of providing sub-scab access comprising:
   providing a sterile scab separation device within a first end opening of a sterility cover;
   releasably securing a needle at an end opening of the sterility cover opposite the first end opening;
   separating the scab separation device and the sterility cover while keeping the sterility cover secured to the needle to continue to maintain sterility of the needle while the scab separation device is used for directing a terminal point of the scab separation device against an interface between a scab and a patient's flesh at an access site; and
   separating at least a portion of the scab from the patient's flesh at the access site.

2. The method of claim 1 including frictionally securing the scab separation device with the sterility cover prior to use.

3. The method of claim 1 including:
   providing a lifting surface adjacent the terminal point; and
   frictionally securing the scab separation device with the sterility cover prior to use with the lifting surface and terminal point within the sterility cover.

4. The method of claim 1 wherein the separating at least a portion of the scab includes lifting the scab away from the access site via a lifting surface formed proximate the terminal point on the scab separation device.

5. The method of claim 1 wherein the separating the scab separation device includes utilizing a grip portion, the method further including manipulating the scab separation device via the grip portion.

6. The method of claim 5 wherein the grip portion is disposed outside of the sterility cover, the method including the removing the scab separation device from the sterility cover by gripping the grip portion.

7. The method of claim 1 wherein the providing the scab separation device includes providing a series of surfaces of differing inclinations thereon, and the separating at least a portion of the scab includes inserting the scab separation device under the scab whereby the series of surfaces lifts the scab to assist in scab separation.

8. The method of claim 1 further including:
   providing the scab separation device with a hub portion; and
   maintaining the scab separation device with the sterility cover with cooperating structure between the hub portion and the sterility cover.

9. The method of claim 1 further including providing the needle with a tubing connected for fluid communication from the patient through the needle and into the tubing.

10. The method of claim 9 wherein the needle includes an arterio-venous fistula.

11. The method of claim 1 including:
    providing a first cavity portion in the sterility cover for receiving the scab separation device therein;
    providing a second cavity portion in the sterility cover for receiving the needle therein; and
    providing a barrier between the first and second cavity portions to at least partially maintain sterility therebetween when one of the scab separation device or needle is removed exposing its respective cavity portion to the environment.

12. The method of claim 1, wherein the sterility cover is an extrusion-formed cylinder having a uniform diameter and wherein the method includes inserting the scab separation device to seal an end of the cylinder.

13. A method of providing sub-scab access comprising:
    providing a needle set, the needle set including:
      a tube set;
      a needle hub secured with the tube set;
      a needle secured with the needle hub and in fluid communication with the tube set;
      a sterility cover releasably secured with the needle hub for maintaining sterility of the needle, and
      a scab separation device releasably secured with the sterility cover, the sterility cover maintaining sterility of an operative portion of the scab separation device;
    removing the scab separation device from the sterility cover while keeping the sterility cover secured to the needle hub to continue to maintain sterility of the needle while the scab separation device is used for directing the operative portion of the scab separation device against an interface between a scab and a patient's flesh at an access site;
    separating at least a portion of the scab from the patient's flesh at the access site;
    removing the sterility cover from the needle hub to expose the needle;
    inserting the needle in the access site; and
    disposing of the scab separation device.

14. The method of claim 13 wherein the sterility cover is an extrusion-formed cylinder having a uniform diameter, which diameter is selected to engage frictionally with the scab separation device and the needle hub.

15. A method of providing sub-scab access comprising:

providing a sterile scab separation device within a first end opening of a sterility cover;

releasably securing a needle at an end opening of the sterility cover opposite the first end opening to form a needle assembly and providing the needle assembly packaged for a procedure;

opening a package of the needle assembly;

separating the scab separation device and the sterility cover;

directing a terminal point of the scab separation device against an interface between a scab and a patient's flesh at an access site; and separating at least a portion of the scab from the patient's flesh at the access site.

* * * * *